US007196228B2

(12) United States Patent
Wolf et al.

(10) Patent No.: US 7,196,228 B2
(45) Date of Patent: Mar. 27, 2007

(54) MULTIMER FORMS OF MONO-AND BIS-ACYLPHOSPHINE OXIDES

(75) Inventors: Jean-Pierre Wolf, Maisprach (CH); Gebhard Hug, Rheinfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 96 days.

(21) Appl. No.: 10/517,231

(22) PCT Filed: Jun. 3, 2003

(86) PCT No.: PCT/EP03/05801

§ 371 (c)(1),
(2), (4) Date: Dec. 7, 2004

(87) PCT Pub. No.: WO03/104245

PCT Pub. Date: Dec. 18, 2003

(65) Prior Publication Data

US 2005/0245768 A1    Nov. 3, 2005

(30) Foreign Application Priority Data

Jun. 11, 2002    (EP) ................... 02405473

(51) Int. Cl.
*C07F 9/02*    (2006.01)
(52) U.S. Cl. .......................... 568/14; 568/15
(58) Field of Classification Search ................ 568/15
See application file for complete search history.

(56) References Cited

U.S. PATENT DOCUMENTS

| 4,324,744 | A | | 4/1982 | Lechtken et al. | ............ 260/932 |
| 4,710,523 | A | * | 12/1987 | Lechtken et al. | ............. 522/14 |
| 5,218,009 | A | * | 6/1993 | Rutsch et al. | .................. 522/14 |
| 5,410,060 | A | | 4/1995 | Schroeder et al. | ............ 546/21 |
| 5,723,512 | A | * | 3/1998 | Leppard et al. | ................ 522/55 |
| 6,399,805 | B2 | * | 6/2002 | Wolf et al. | .................. 556/405 |
| 6,737,549 | B2 | | 5/2004 | Wolf et al. | .................... 568/14 |
| 2001/0031898 | A1 | | 10/2001 | Wolf et al. | .................... 568/13 |
| 2005/0004247 | A1 | | 1/2005 | Wolf et al. | ..................... 522/8 |

FOREIGN PATENT DOCUMENTS

| DE | 2245817 | 3/1974 |
| EP | 0007508 | 2/1980 |
| EP | 0413657 | 2/1991 |
| EP | 0601413 | 6/1994 |

OTHER PUBLICATIONS

A. R. Barron et al, Journal of the Chemical Society, vol. 23, (1987), pp. 1753-1754.

L. Macarie et al., Revista de Chimie, vol. 53, No. 7, (2002), pp. 568-571.

Derwent Abstract 2516V/14 for DE 2245817 (1974).

* cited by examiner

*Primary Examiner*—Thurman K. Page
*Assistant Examiner*—Chukwuma Nwaonicha
(74) *Attorney, Agent, or Firm*—Joseph C. Suhadolnik

(57) ABSTRACT

The invention relates to dimer and multimer form of BAPO compounds of the formula (I) dimer and multimer forms of MAPO compounds of the formula (II) wherein $R_1$, $R_2$, and $R_3$ independently of one another are unsubstituted or substituted $C_1$–$C_{12}$alkyl, benzyl, $C_1$–$C_{12}$alkoxy, $C_3$–$C_6$cycloalkyl or $C_5$–$C_{14}$aryl; Q is a di- tri or tetravalent arylene residue; n is 1–4, m is 0–2, n+m is 2, 3 or 4, with the proviso, that $R_1$ and $R_3$ are different from each other. The invention further relates to a process for the preparation of dimer or multimer forms of BAPO compounds of the formula (I) and of dimer or multimer forms of MAPO compounds of the formula (II), characterized in the (n+m) equivalents of a dimetalated-phosphine $R_1P(M)_2$ is reacted with one equivalent of a di- or polycarboxylic acid halogenide to form an intermediate of the formula III the intermediate is then reacted either with (n+m) equivalents of a further carboxylic acid halogenide ($R_2$—CO-Hal) or with a halogenide $R_3$-Hal, the reaction products are then oxidized to form phosphine oxides of the formula I or II

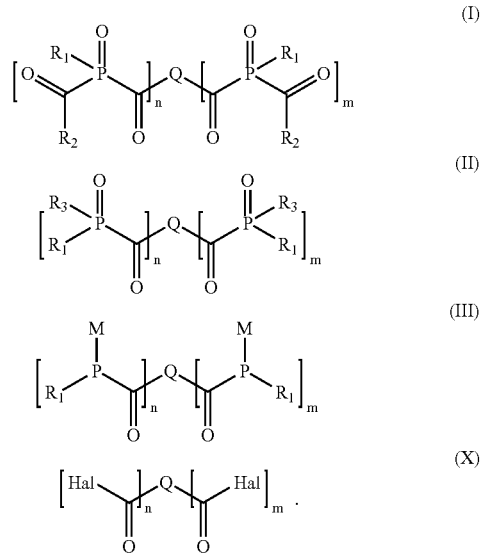

2 Claims, No Drawings

MULTIMER FORMS OF MONO-AND BIS-ACYLPHOSPHINE OXIDES

The present invention relates to new dimer and multimer forms of monoacylphosphine oxides (MAPO), bisacylphosphine oxides (BAPO), to new cyclic forms of bisacyl phosphine oxides (BAPO), to a process for their preparation and to new acylphosphine compounds obtained as intermediates in said process.

The preparation of dimer forms of monoacylphosphine oxides of the general formula

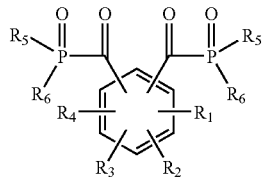

has been described in the European Patent Publication EP-A 0 601 413. Said process is characterized in that an arene-bisacyl chloride is reacted with e.g. an alkoxy-diphenyl-phosphine. The compounds obtained are due to the alkoxy-diphenylphosphine reactant symmetric dimer forms of monoacylphosphine oxides, i.e. the residue $R_5=R_6$. Concerning asymmetric forms one of the residues $R_5$ or $R_6$ must be an alkoxy group.

The U.S. Patent Publication 2001/0031898 describes the preparation of monomer forms of bisacylphosphine oxides

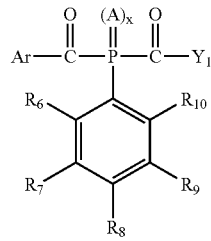

by reacting an acyl halide Ar—CO—X with a dimetalated phosphine $RP(M)_2$ and subsequent reaction of the product obtained with an acyl halide. Dimer forms of BAPO compounds are encompassed by the general definition of the compounds described in U.S. Patent Publication 2001/0031898 but they have not been actually and explicitly disclosed in this patent publication, nor the preparation thereof has been exemplified.

There is still a need to find a method for preparing both, dimer and multimer symmetric and asymmetric forms of BAPO and MAPO compounds as well as cyclic forms of BAPO compounds, whereby said method should, in case of MAPO compounds, have a broad latitude in the choice of substituents on the phosphor atom.

In one aspect the invention relates to dimer and multimer forms of BAPO compounds of the formula I

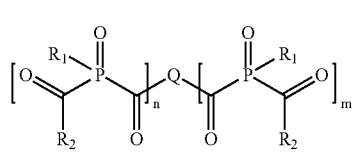

wherein $R_1$ is unsubstituted or substituted $C_1$–$C_{12}$alkyl, benzyl, $C_1$–$C_{12}$alkoxy, $C_3$–$C_6$cycloalkyl or $C_5$–$C_{14}$aryl;

$R_2$ is unsubstituted or substituted $C_3$–$C_6$cycloalkyl or $C_5$–$C_{14}$aryl;

Q is a di-tri or tetravalent arylene residue;

n is 1–4, m is 0–2, n+m is 2, 3 or 4.

The invention further relates to dimer and multimer forms of MAPO compounds of the formula II

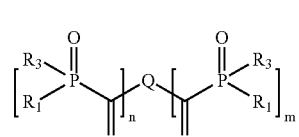

wherein $R_1$ and $R_3$ independently of one another are unsubstituted or substituted $C_1$–$C_{12}$alkyl, benzyl, $C_1$–$C_{12}$alkoxy, $C_3$–$C_6$cycloalkyl or $C_5$–$C_{14}$aryl;

Q is a di-tri or tetravalent arylene residue;

n is 1–4, m is 0–2, n+m is 2, 3 or 4;

with the proviso, that $R_1$ and $R_3$ are different from each other.

The invention further relates to a process for the preparation of dimer or multimer forms of BAPO compounds of the formula I and of dimer or multimer forms of MAPO compounds of the formula II, characterized in that (n+m) equivalents of a dimetalated-phosphine $R_1P(M)_2$ are reacted with one equivalent of a di- or polycarboxylic acid halogenide

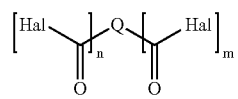

to form an intermediate of the formula III

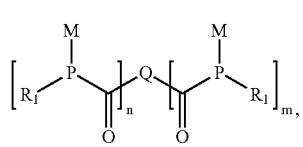

the intermediate is then reacted either with (n+m) equivalents of a further carboxylic acid halogenide ($R_2$—CO-Hal) to form dimer or multimer forms of bisacylphosphine-intermediates of the formula IV

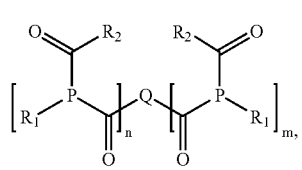

or with a halogenide $R_3$-Hal to form dimer or multimer forms of monoacylphosphine intermediates of the formula V

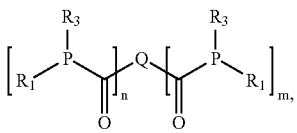

said phosphines IV or V are then oxidized to form phosphine oxides of the formula I or II, wherein M is Li, Na or K and $R_1$, $R_2$ and $R_3$; Q, n and m are as defined above.

The intermediate compounds of the formula III are novel and are also part of the invention. Thus, the invention further relates to compounds of the formula III as defined above. The compounds of the formula III are identified by $^{31}$P-NMR spectroscopy and are stable in solution under inert gas at room temperature for a number of weeks.

The invention further relates to cyclic forms of BAPO compounds of the formula VI and VII

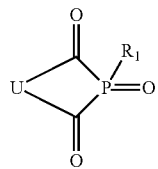

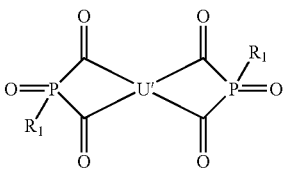

wherein
$R_1$ is unsubstituted or substituted $C_1$–$C_{12}$alkyl, benzyl, $C_1$–$C_{12}$alkoxy, $C_3$–$C_6$cycloalkyl or $C_5$–$C_{14}$aryl;
U is a divalent arylene residue and U' is a tetravalent arylene residue.

The invention further relates to a process for the preparation of cyclic forms of BAPO compounds of the formula VI characterized in that one equivalent of a dimetalated-phosphine $R_1P(M)_2$ is reacted with one equivalent of a dicarboxylic acid halogenide

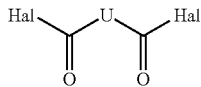

to form an intermediate of the formula III'

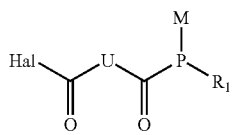

said intermediate cyclizes and is then oxidized to form phosphine oxides of the formula VI wherein $R_1$, M and U are as defined above.

The invention further relates to a process for the preparation of cyclic forms of BAPO compounds of the formula VII characterized in that two equivalent of a dimetalated-phosphine $R_1P(M)_2$ are reacted with one equivalent of a tetracarboxylic acid halogenide

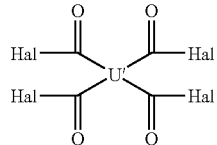

to form an intermediate of the formula III''

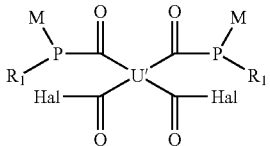

said intermediate cyclizes and is then oxidized to form phosphine oxides of the formula VII wherein $R_1$, M and U' are as defined above.

Preference is given to using compounds of the formula I or II in which n is 1 and m is 1.

Definitions $C_1$–$C_{12}$alkyl is linear or branched and is, for example, $C_1$–$C_{12}$alkyl, $C_1$–$C_8$alkyl, $C_1$–$C_6$alkyl or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl. The alkyl groups may be interrupted once or more than once by O, S or N($C_1$–$C_{12}$alkyl). If the radicals are interrupted by two or more O, S or N($C_1$–$C_{12}$alkyl) then the O atoms, S atoms or N($C_1$–$C_{12}$alkyl) groups are in each case separated from one another by at least one methylene group. The O atoms, S atoms or N($C_1$–$C_{12}$alkyl) groups are thus not directly consecutive. For example, structural units such as —CH$_2$—O—CH$_3$, —CH$_2$CH$_2$—O—CH$_2$CH$_3$, —[CH$_2$CH$_2$O]$_z$—CH$_3$, where z=1 to 9, —(CH$_2$CH$_2$O)$_7$CH$_2$CH$_3$, —CH$_2$—CH(CH$_3$)—O—CH$_2$—CH$_2$CH$_3$, —CH$_2$—CH(CH$_3$)—O—CH$_2$—CH$_3$, —CH$_2$SCH$_3$ or —CH$_2$—N(CH$_3$)$_2$ arise.

The alkyl groups may be mono- or polysubstituted by $C_1$–$C_{12}$ alkyl; $C_1$–$C_{12}$ alkoxy, —S—$C_1$–$C_{12}$alkyl, phenyl, phenoxy, —COO$C_1$–$C_{12}$alkyl, —COO—$C_5$–$C_{14}$aryl or CN.

As used herein, the term "$C_1$–$C_{12}$alkoxy" refers to a group O—$C_1$–$C_{12}$alkyl, wherein the alkyl radical is as described above.

Examples of $C_3$–$C_6$cycloalkyl groups are cyclopropyl, cyclobutyl, cyclopentyl, cyclohexyl. The $C_3$–$C_6$cycloalkyl groups may be substituted by $C_1$–$C_{12}$ alkyl, $C_1$–$C_{12}$ alkoxy, —S—$C_1$–$C_{12}$alkyl, phenyl, phenoxy, —COO$C_1$–$C_{12}$alkyl, —COO—$C_5$–$C_{14}$aryl or CN. Examples are 2,4,6-trimethylcyclohexyl, 2,6-dimethylcyclohexyl and 2,6-dimethoxycyclohexyl.

$C_5$–$C_{14}$aryl is phenyl, naphthyl, biphenyl, anthracyl and the like.

The aryl radicals may be mono or polysubstituted by halogen, phenyl, $C_1$–$C_{12}$alkyl and/or $C_1$–$C_{12}$alkoxy, —S—$C_1$–$C_{12}$alkyl,  CF$_3$,  Cl,  —N($C_1$–$C_{12}$alkyl)$_2$  or —N($C_{1-C12}$alkyl interrupted by O)$_2$.

Examples are:

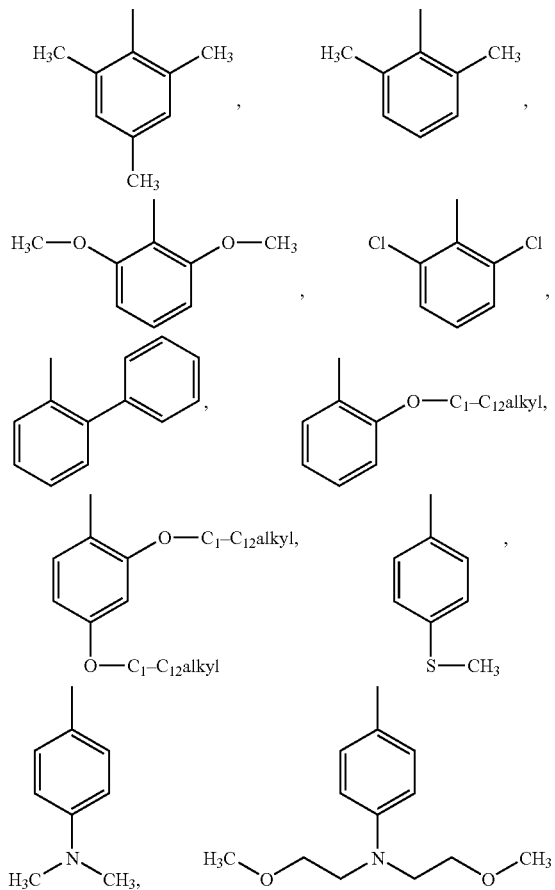

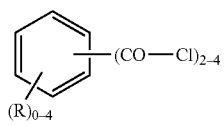

Q is a di-tri or tetravalent arylene residue derived from the following di or polycarboxylic acid halogenides, preferably chlorides.

Compounds of the Formula A

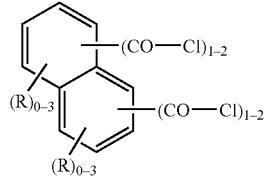

wherein
R is $C_1$–$C_{12}$alkyl, $C_1$–$C_{12}$alkoxy, $C_1$–$C_{12}$alkylthio, $C_5$–$C_{14}$aryl, O—$C_5$–$C_{14}$aryl, halogen, NH($C_1$–$C_{12}$alkyl), N($C_1$–$C_{12}$alkyl)$_2$, C(O)O($C_1$–$C_{12}$alkyl), CO—NH($C_1$–$C_{12}$alkyl), CO—N($C_1$–$C_{12}$alkyl)$_2$ or CF$_3$ Commercial compounds of the formula A are:
Phthalic acid and derivatives thereof such as, for example, tetrafluoro- or tetrachloro phthalic acid, 3-fluorophthalic acid, 4-(trifluoromethyl)phthalic acid, 4-chloro- or 4,5-dichlorophthalic acid, 4-methylphthalic acid;
Hemimellitic-, trimellitic- and pyromellitic acid;
Isophthalic acid and derivatives thereof such as, for example, tetrafluoroisophthalic acid, 4-bromoisophthalic acid, 4-hydroxy- or 5-hydroxyisophthalic acid, 5-aminoisophthalic acid;
Trimesic acid, 5-methyl-1,3-benzenedicarboxylic acid;
Therephthalic acid and derivatives thereof such as, for example, tetrafluoro- or tetrachloro-terephthalic acid, 2-bromoterephthalic acid, 2-aminoterephthalic acid, 2,5-dimethyl-terephthalic acid, 2,5-dichloro- or 2,5-dibromo-terephthalic acid.

Compounds of the Formula B

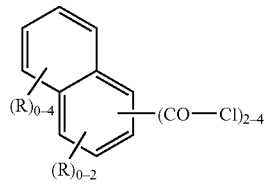

wherein R is as defined in formula A.
Commercial compounds of the formula B are 1,4,5,8-naphthalene tetracarboxylic acid or 1,4,5,8-naphthalene tetracarboxylic acid hydrate.

Compounds of the Formula C

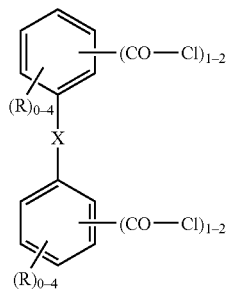

wherein R is as defined in formula A.
Commercial compounds of the formula C are 2,3-naphthalenedicarboxylic acid or 1,4-naphthalene dicarboxylic acid.

Compounds of the Formula D

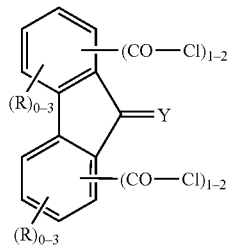

wherein R is as defined in formula A and X is a bond, —O—, —S—, methylene, —CH(CH$_3$)—, —C(CH$_3$)$_2$—, —C(CF$_3$)$_2$—, —C(O)—, —S(O)— or —S(O)$_2$—.
Commercial compounds of the formula D are 3,3',4,4'-benzophenonetetracarboxylic acid, 2,3,2'-biphenyltricarboxylic acid or 4,4'(hexafluoroisopropylidene)phthalic acid.

Compounds of the Formula E

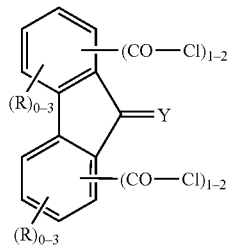

wherein R is as defined in formula A and Y is H$_2$, O, S or CH$_2$.

Commercially available is 9-fluorenone-2,7-dicarboxylic acid

Compounds of the Formula F or G

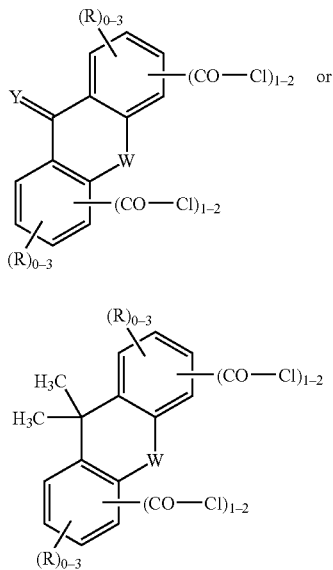

wherein R and Y are as defined above, and W is O, S, $CH_2$ or $N(C_1$–$C_{12}$alkyl).

Commercially available is 2,7-di-tert-butyl-9,9-dimethyl-4,5-xanthenedicarboxylic acid.

Compounds of the Formula H, I, J, K, L, M, N or O.

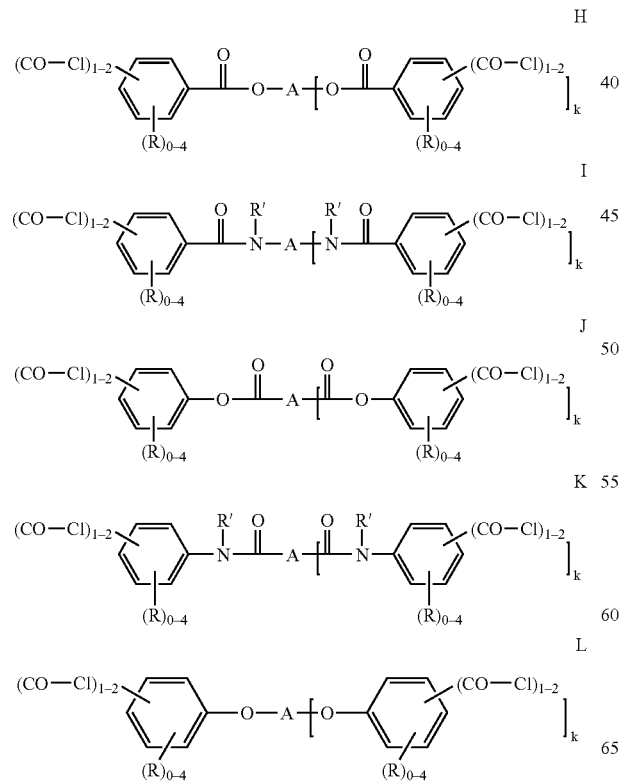

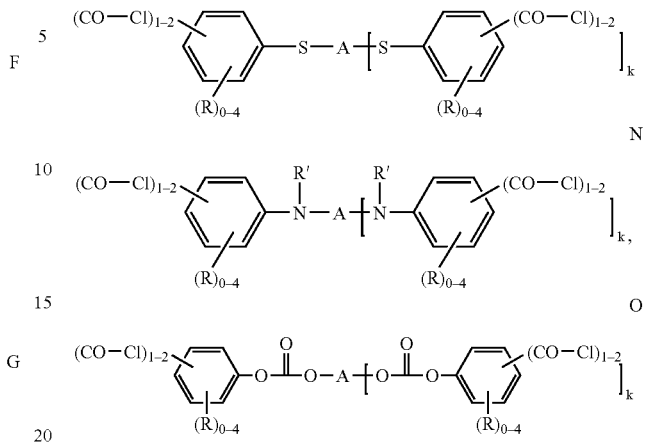

wherein
k is 1–3,
R is as defined above,
R' is hydrogen, phenyl, $C_1$–$C_{12}$ alkyl or $C_3$–$C_6$cycloalkyl,
A is selected from $C_5$–$C_{14}$arylene, $C_3$–$C_6$cycloalkylene or bicycloalkylene, linear or branched $C_2$–$C_{24}$alkylene optionally interrupted once or more than once by non-consecutive —O— or —S— atoms or by groups selected from —CO—, —COO—, —OCO—, —O—COO—, phenylene, $C_5$–$C_{14}$arylene, $C_3$–$C_6$cycloalkylene, —CH=CH—, bicycloalkylene, biphenylene, —Si(CH$_3$)$_2$—, —Si(CH$_3$)$_2$—O—Si(CH$_3$)$_2$— or —CF$_2$—.

The group A may be substituted by $C_1$–$C_{12}$alkyl, $C_1$–$C_{12}$alkoxy, —S—$C_1$–$C_{12}$alkyl, phenyl, phenoxy, —O—CO$C_1$–$C_{12}$alkyl, —O—CO$C_5$–$C_{14}$aryl, —COO$C_1$–$C_{12}$alkyl, —COO—$C_5$–$C_{14}$aryl, CN, CF$_3$, F or Cl.

Concerning cyclic forms of BAPO compounds of the formula VI
U is a divalent arylene residue derived from the following dicarboxylic acid halogenides, preferably chlorides, U1–U4

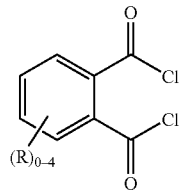

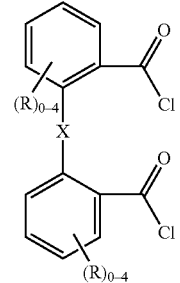

-continued

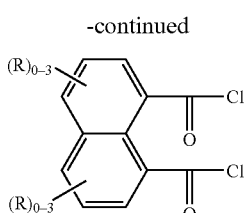
U3

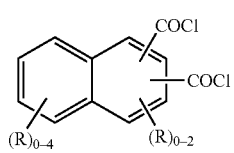
U4 wherein R and X are as defined above.

Concerning cyclic forms of BAPO compounds of the formula VII
U' is a tetravalent arylene residue derived from the following tetracarboxylic acid halogenides, preferably chlorides, U5 and U6

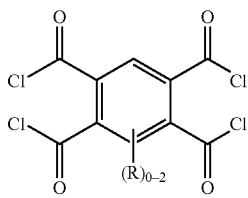
U5

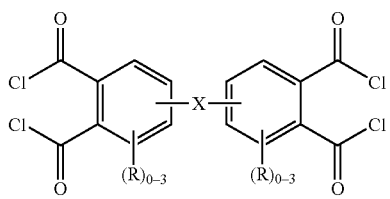
U6

The Process Starting Compounds:

The preparation of the metalated phosphines $R_1P(M)_2$ can, for example, be carried out by reacting suitable phosphorus halides $R_1P(Hal)_2$ (preparation of which is known and disclosed, for example, by W. Davies in J. Chem. Soc. (1935), 462 and J. Chem. Soc. (1944), 276 with the corresponding alkali metal. Suitable as metal (M) are lithium, sodium or potassium. Lithium is preferred. The use of mixtures of these metals is also possible. 4 to 8 molar equivalents of the alkaline metal are advantageously used. The reaction is advantageously carried out in a solvent. In particular, as solvents, it is possible to use ethers which are liquid at atmospheric pressure and, room temperature. Examples are dimethyl ether, diethyl ether, methyl propyl ether, 1,2-dimethoxyethane, bis(2-methoxyethyl) ether, dioxane or tetrahydrofuran. Preference is given to using tetrahydrofuran. The reaction temperatures are advantageously −60° C. to +120° C.

Another conceivable method for the preparation of metalated phosphines is, for example, the reaction of suitable phosphines $R_1P(H)_2$ with the corresponding alkali metal hydride or an alkyllithium compound with the exclusion of air in an inert solvent at temperatures of e.g. −80° C. to +120° C. Advantageously, 2 to 4 mol equivalents of the alkali metal hydrides or alkyllithium compound are used. Suitable solvents are e.g. ethers as described above, or inert solvents, such as alkanes, cycloalkanes, or aromatic solvents such as toluene, xylene, mesitylene.

Suitable aryl phosphines can be prepared by reduction of the corresponding aryldichloro-phosphines [Ar—P—$Cl_2$], arylphosphonic esters [Ar—P—O(OR')$_2$) and arylphosphonous esters [Ar—P(OR')$_2$] using $LiAlH_4$; $SiHCl_3$; $Ph_2SiH_2$ (Ph=phenyl): a) LiH, b) $H_2O$;

a) Li/tetrahydrofuran, b) $H_2O$ or a) Na/toluene, b) $H_2O$. These methods are described, for example, in U.S. Pat. No. 6,020,528 (col. 5–6). Hydrogenations using $LiAlH_4$ are given, for example, in Helv. Chim. Acta 1966, No. 96, 842.

The di- or poly carboxylic acid halogenides used as starting material are known substances, some of which are available. Examples are listed above.

Carboxylic acid chlorides which are not commercially available may be prepared starting from the corresponding carboxylic acids using known reactions. The corresponding carboxylic acids may be prepared as follows.

Compounds H: by reaction of an anhydride with a di-, tri- or tetrafunctional alcohol.

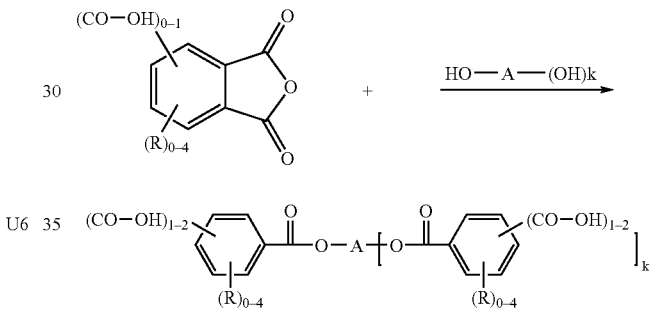

Compound I: by reaction of an anhydride with a di-, tri- or tetrafunctional amine.

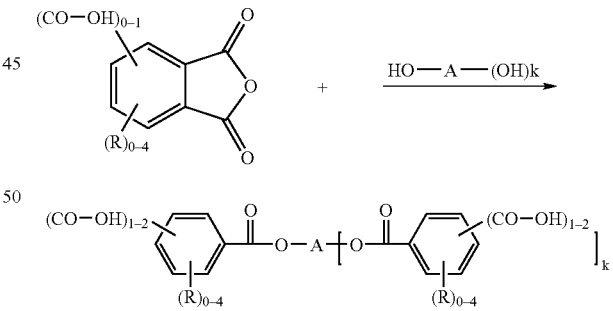

Suitable anhydrides are, for example, phthalic anhydride, hemimellitic anhydride, trimellitic anhydride, tetrafluorophthalic anhydride or 4,5-dichlorophthalic anhydride.

Compound J: by transesterification of a hydroxy carboxylic acid with a di-, tri- or tetra-functional ester.

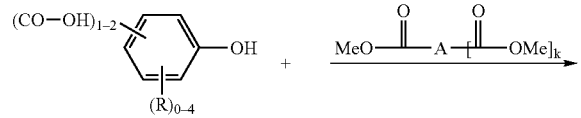

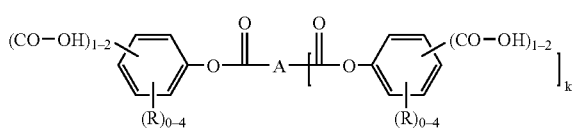

Suitable hydroxy carboxylic acids are, for example, 4-hydroxyphthalic acid, 5-hydroxyisophthalic acid, 3-hydroxy- or 4-hydroxybenzoic acid or salicylic acid.

Compound K: by reaction of an aminocarboxylic acid with a di-, tri- or tetrafunctional acid chloride

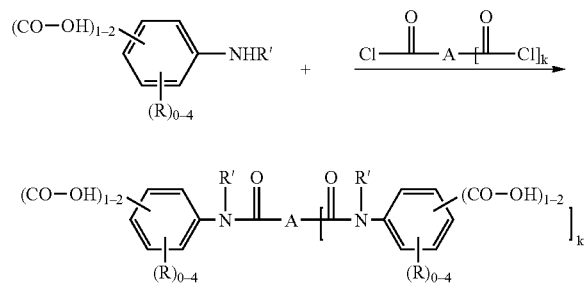

Suitable aminocarboxylic acids are, for example, 3-amino- or 4-aminophthalic acid, 5-aminoisophthalic acid, 2-aminoterephphthalic acid, antranilic acid, 3-amino- or 4-aminobenzoic acid.

Compounds L, M or N: by reaction of a halogen substituted carboxylic acids with a di-, tri- or tetrafunctional alcohol, amine or thiol

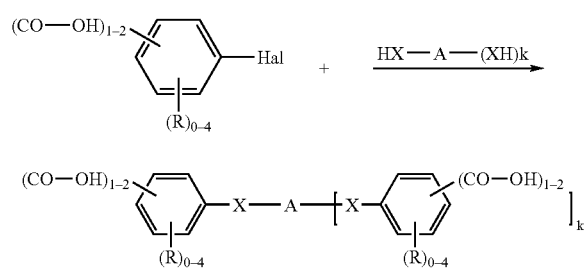

X=O, S, NR'

Suitable halogen substituted carboxylic acids are, for example, 3-fluoro- or 4-chlorophthalic acid, 2-fluoroisophthalic acid, 2-fluoro- or 4-fluorobenzoic acid or 4-chlorobenzoic acid.

Compound O: by reaction of a hydroxy carboxylic acid with a di-, tri- or tetrafunctional chloroformiate.

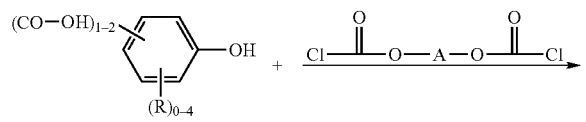

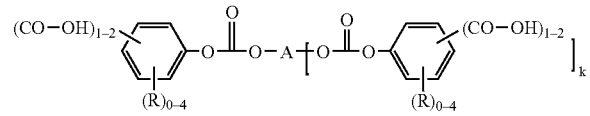

Suitable hydroxy carboxylic acids are, for example, 4-hydroxyphthalic acid, 5-hydroxyisophthalic acid, 3-hydroxy- or 4-hydroxybenzoic acid, salicylic acid.

Cyclic forms of Bapo compounds may be prepared starting from the following dicarboxylic acid chlorides of the formula U1: phthalic acid, tetrafluorophthalic acid, 4,5-dichlorophthalic acid, 4-hydroxy-, 3-fluoro- or 4-chloro phthalic acid; of the formula U2 2,2-oxydibenzoic acid or diphenic acid; of the formula U3 naphthalene-1,8-dicarboxylic acid; of the formula U4 2,3-naphthalene dicarboxylic acid; or starting from the following tetracarboxylic acids: 3,3',4,4'-benzophenone tetracarboxylic acid or 4,4'-(hexafluoroisopropylidene)diphthalic acid.

Inventive Process

The process starts by reacting a carboxylic acid halogenide with a metalated phosphine preferably in an inert solvents such as THF, dioxane or diethylether at a temperature from −20 to 80° C.

An important feature of the process for preparing dimer or multimer forms of BAPO or MAPO compounds comprises the control of the mole ratio of metalated phosphine to di- or poly-carboxylic acid chloride. It is desirable that about one equivalent of metalated phosphine groups be available per equivalent of acid chloride groups. The carboxylic acid chloride is preferably dropped into the phosphine in order to maintain an excess of the phosphine. Using about 0.5 equivalents of metalated phosphine groups per equivalent of acid chloride groups results in cyclic bisacylphosphine oxides.

The reaction between the di- or polycarboxylic acid chloride and the metalated phosphine produces an intermediate having the structural formula III.

To prepare MAPO compounds the intermediate is treated with an alkyl or aryl halogenide resulting in P-alkylation of the phosphine. The alkylating agent is added slowly. The reaction is preferably carried out in the same solvent and temperature range as in the first reaction step providing the intermediate.

To prepare BAPO compounds the intermediate is treated with another carboxylic acid halogenide resulting in P-acylation of the phosphine. The acylating agent is added slowly. The reaction is carried out in the same solvent and temperature range as in the first reaction step providing the intermediate.

The oxidation of the phosphine is carried out using oxidizing agents customary in the art. Suitable oxidizing agents are, for example, hydrogen peroxide, air or pure oxygen.

Use

The MAPO and BAPO compounds of the formula I and II as well as the cyclic BAPO compounds of the formula VI or VII can be used as photoinitiators for the photo-polymerization of ethylenically unsaturated compounds or mixtures which comprise such compounds. This use can also take place in combination with other photoinitiators and/or other additives.

Thus, the invention also relates to a photopolymerizable composition comprising
(a) at least one ethylenically unsaturated photopolymerizable compound, and
(b) as photoinitiator, at least one compound of the formula I, II, VI or VII as defined above.

The unsaturated compounds can contain one or more olefinic double bonds. They can be of low molecular weight (monomeric) or relatively high molecular weight (oligomeric). Examples of monomers with a double bond are alkyl or hydroxyalkyl acrylates or methacrylates, for example methyl acrylate, ethyl acrylate, butyl acrylate, 2-ethylhexyl acrylate or 2-hydroxy-ethyl acrylate, isobornyl acrylate, methyl methacrylate or ethyl methacrylate. Also of interest are silicon- or fluorine-modified resins, e.g. silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halostyrenes, N-vinylpyrrolidone, vinyl chloride or vinylidene chloride.

Examples of monomers having two or more double bonds are ethylene glycol diacrylate, propylene glycol diacrylate, neopentyl glycol diacrylate, hexamethylene glycol diacrylate or bisphenol A diacrylate, 4,4'-bis(2-acryloyloxyethoxy) diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of higher molecular weight (oligomeric) polyunsaturated compounds are acrylicized epoxy resins, polyurethanes, polyethers and polyesters which are acrylicized or contain vinyl ether or epoxy groups. Further examples of unsaturated oligomers are un-saturated polyester resins which are mostly prepared from maleic acid, phthalic acid and one or more diols and have molecular weights of from about 500 to 3,000. In addition, it is also possible to use vinyl ether monomers and oligomers, and maleate-terminated oligomers having polyester, polyurethane, polyether, polyvinyl ether and epoxy main chains. In particular, combinations of oligomers which carry vinyl ether groups and polymers as described in WO 90/01512 are highly suitable. However, copolymers of vinyl ether and maleic acid-functionalized monomers are also suitable. Such unsaturated oligomers may also be referred to as prepolymers.

Examples of particularly suitable compounds are esters of ethylenically unsaturated carboxylic acids and polyols or polyepoxides, and polymers containing ethylenically unsaturated groups in the chain or in side-groups, for example unsaturated polyesters, polyamides and polyurethanes and copolymers thereof, alkyd resins, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic acid, methacrylic acid, crotonic acid, itaconic acid, cinnamic acid, unsaturated fatty acids such as linolenic acid or oleic acid. Preference is given to acrylic acid and methacrylic acid.

Suitable polyols are aromatic and, in particular, aliphatic and cycloaliphatic polyols. Examples of aromatic polyols are hydroquinone, 4,4'-dihydroxydiphenyl, 2,2-di(4-hydroxy-phenyl)propane, and also novolaks and resols. Examples of polyepoxides are those based on said polyols, particularly aromatic polyols and epichlorohydrins. In addition, polymers and copolymers which contain hydroxyl groups in the polymer chain or in side groups, for example polyvinyl alcohol and copolymers thereof or hydroxyalkyl polymethacrylates or copolymers thereof, are also suitable as polyols. Further suitable polyols are oligoesters containing hydroxyl end-groups.

Examples of aliphatic and cycloaliphatic polyols are alkylenediols having, preferably, 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, poly-ethylene glycols having molecular weights of, preferably, 200 to 1,500, 1,3-cyclopentanediol, 1,2-, 1,3- or 1,4-cyclohexanediol, 1,4-dihydroxymethylcyclohexane, glycerol, tris(β-hydroxy-ethyl)amine, trimethylolethane, trimethylolpropane, pentaerythritol, dipentaerythritol and sorbitol.

The polyols may be partially or completely esterified using one or different unsaturated carboxylic acids, where the free hydroxyl groups in partial esters may be modified, e.g. etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol having molecular weights of from 200 to 1,500, or mixtures thereof.

Also suitable as component (a) are the amides of identical or different unsaturated carboxylic acids of aromatic, cycloaliphatic and aliphatic polyamines having, preferably, 2 to 6, particularly 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)ethane or di(β-aminopropoxy)-ethane. Further suitable polyamines are polymers and copolymers with or without additional amino groups in the side chain and oligoamides containing amino end groups. Examples of such unsaturated amides are: methylenebisacrylamide, 1,6-hexamethylenebisacrylamide, diethylenetriaminetrismethacrylamide, bis(methacrylamidopropoxy)ethane, β-methacryl-amidoethyl methacrylate, N[(β-hydroxyethoxy)ethyl]acrylamide.

Suitable unsaturated polyesters and polyamides are derived, for example, from maleic acid and diols or diamines. The maleic acid may be replaced by other dicarboxylic acids. They can be used together with ethylenically unsaturated comonomers, e.g. styrene. The poly-esters and polyamides may also be derived from dicarboxylic acids and ethylenically unsaturated diols or diamines, particularly from relatively long chain compounds containing, for example, 6 to 20 carbon atoms. Examples of polyurethanes are those constructed from saturated or unsaturated diisocyanates and unsaturated or saturated diols.

Polybutadiene and polyisoprene and copolymers thereof are known. Suitable comonomers are, for example, olefins, such as ethylene, propene, butene, hexene, (meth)acrylates, acrylonitrile, styrene or vinyl chloride. Polymers containing (meth)acrylate groups in the side chain are likewise known. These may, for example, be products of the reaction of novolak-based epoxy resins with (meth)acrylic acid, homo- or copolymers of vinyl alcohol or hydroxy-alkyl derivatives thereof which have been esterified using (meth)acrylic acid, or homo- and copolymers of (meth)acrylates which have been esterified using hydroxyalkyl(meth)acrylates.

The photopolymerizable compounds may be used on their own or in any desired mixtures. Preference is given to using mixtures of polyol (meth)acrylates.

It is also possible to add binders to the compositions according to the invention; this is particularly advantageous if the photopolymerizable compounds are liquid or viscose substances. The amount of binder may, for example, be 5–95% by weight, preferably 10–90% by weight and particularly 40–90% by weight, based on the total solids. The binder is chosen depending on the field of application and on the properties required therefore, such as the facility for development in aqueous or organic solvent systems, adhesion to substrates and sensitivity to oxygen.

Examples of suitable binders are listed in U.S. Patent Publication 2001/0031898 which publication is included in the present Application by reference.

Apart from the photoinitiator, the photopolymerizable mixtures can also contain various additives such as thermal inhibitors, compounds to increase the storage stability, light protection agents such as for example the following light protection agents listed in US Patent Publication 2001/0031898

2-(2'-Hydroxyphenyl)benzotriazoles, 2-hydroxybenzophenones, esters of unsubstituted or substituted benzoic acids, acrylates, sterically hindered amines, oxalamides, 2-(2-hydroxy-phenyl)-1,3,5-triazines, phosphites and phosphonites.

The photopolymerizable mixtures can also contain photosensitizers such as for example the following photosensitizers listed in U.S. Patent Publication 2001/0031898: Triethanolamine, N-methyldiethanolamine, ethyl p-dimethylaminobenzoate or Michlers ketone, benzophenone, thioxanthone, in particular also isopropylthioxanthone, anthraquinone and 3-acylcoumarin derivatives, terphenyls, styryl ketones, and 3-(aroyl-methylene)thiazolines, camphorquinone, but also eosin, rhodamine and erythrosine dyes.

Depending on the intended use, further customary additives are optical brighteners, fillers, pigments, both white and coloured pigments, dyes, antistats, wetting agents or levelling auxiliaries.

The choice of additives depends on the field of application in question and the properties desired for this field. The above-described additives are customary in the art and are accordingly used in amounts customary in the art. Concrete examples for possible additives are given in US Patent Publication 2001/0031898

In certain cases, it may be advantageous to use mixtures of two or more of the photoinitiators according to the invention. It is of course also possible to use mixtures with known photoinitiators.

The photopolymerizable compositions advantageously comprise the photoinitiator in an amount of from 0.05 to 20% by weight, e.g. 0.05 to 15% by weight, preferably 0.1 to 5% by weight, based on the composition. The amount of photoinitiator stated is based on the total of all added photoinitiators if mixtures thereof are used.

The photopolymerizable compositions can be used for various purposes, for example as printing inks, such as screen printing inks, flexographic printing inks or offset printing inks, as clearcoats, as colour coats, as white coats, e.g. for wood or metal, as powder coatings, as paints, inter alia for paper, water, metal or plastic, as daylight-curable coatings for marking buildings and roads, for photographic reproduction processes, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as photoresists, e.g. galvanoresists, etch or permanent resists, both liquid and dry films, as photostructurable dielectrics, and as solder stopping masks for electronic circuits, as resists for the preparation of colour filters for any type of screen or for producing structures in the production process of plasma displays and electroluminescence displays, for the production of optical switches, optical gratings (interference gratings), for the preparation of three-dimensional objects by mass curing (UV curing in transparent moulds) or by the stereolithography process, as is described, for example, in U.S. Pat. No. 4,575,330, for the preparation of composite materials (e.g. styrenic polyesters which may contain glass fibres and/or other fibres and other auxiliaries) and other thick-layer materials, for the coating or sealing of electronic components or as coatings for optical fibres. The compositions are also suitable for the preparation of optical lenses, e.g. contact lenses and Fresnel lenses, and for the preparation of medical instruments, auxiliaries or implants.

EXAMPLES

1. Preparation of Dimer Bisacylphosphine Oxide. (BAPO)

[Phenyl-(2,4,6-trimethyl-benzoyl)-phosphinoyl]-{2,4,6-trimethyl-3-[phenyl-(2,4,6-trimethyl-benzoyl)-phosphinoanecarbonyl]-phenyl}-methanone

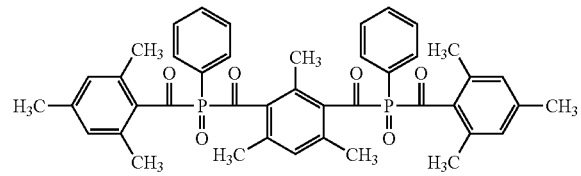

Formula I, $R_1$=phenyl, $R_2$=mesityl, Q=mesitylene, n=1, m=1

120 ml (0.191 mol) buthyllitium were dropped at a temperature of −20° C. to a solution of 10.0 g (0.091 mol) phenylphosphine in 150 ml tetrahydrofurane. A Yellow suspension was obtained. Subsequently 11.2 g (0.0455 mol) 2,4,6-trimethylbenzol-1,3-dicarboxylic acid dichloride diluted with 50 ml tetrahydrofurane were added dropwise at a temperature of 0° C. The reaction mixture was kept at that temperature during 30 min under stirring. Subsequently 16.6 g (0.091 mol) 2,4,6-trimethylbenzoylchloride were added dropwise and stirred at the same temperature for 2 hours. Subsequently the reaction mixture was allowed to reach room temperature. The solvent was rotatory evaporated. The residue is taken up in 200 ml toluene. The solution was diluted with water and the layers were separated. 10.3 g (0.091 mol; 30%) hydrogen peroxide were added to the organic phase. After stirring for 2 h, the organic phase was washed with water and with aqueous saturated NaHCO$_3$, dried over MgSO$_4$ and filtered. Evaporation and Flash column chromatography (eluent: Hexan/ethylacetat 3:1) gave the title compound as a yellow viscous resin. $^{31}$P-NMR 8.30 ppm $^1$H-NMR (ppm) 7.72–7.80 (m), 7.45–7.47 (m), 6.76 (s), 6.62–6.67 (m), 2.11 (s), 2.05 (s), 1.96 (s) und 1.89–1.92 (d) determined in CDCl$_3$.

The following BAPOs may be prepared analogously.

| Ex | Product | Educt | NMR of the Product |
|---|---|---|---|
| 1.a | Formula I, R$_1$ = phenyl, R$_2$ = mesityl, Q = o-phenylene, | Phenylphosphine, Phtaloyldichloride, 2,4,6-Trimethylbenzoyl chloride. | $^{31}$P-NMR 13.12 ppm $^1$H-NMR (ppm) 8.26–8.28 (d), 7.92–7.95 (d), 7.57–7.72 (m), 7.03–7.29 (m), 6.49 (s), 2.06 (s), and 1.60 (s) in CDCl$_3$. Smp. 202–203° C. |
| 1.b | Formula I, R$_1$ = isobutyl, R$_2$ = mesityl, Q = mesitylene. | Isobutylphosphine, 2,4,6-Trimethylbenzol-1,3-dicarboxylic acid chloride, 2,4,6-Trimethylbenzoyl chloride. | $^{31}$P-NMR 29.45 ppm $^1$H-NMR (ppm) 6.87 (s), 6.77–6.78 (d), 1.97–2.20 (m) und 0.96–0.98 (t) in CDCl$_3$. |
| 1.c | Formula I, R$_1$ = phenyl, R$_2$ = mesityl, Q = 3,3′,4,4′,benzophenone-tetrayl. | Phenylphosphine 3,3′,4,4′-benzophenone tetracarboxylic acid dichloride 2,4,6-trimethylbenzoyl chloride | |

2. Preparation of Dimer Monoacylphosphine Oxide. (MAPO)

[3-(Benzyl-isobutyl-phosphinoanecarbonyl)-2,4,6-trimethyl-phenyl]-(benzyl-isobutyl-phosphinoyl)-methanone

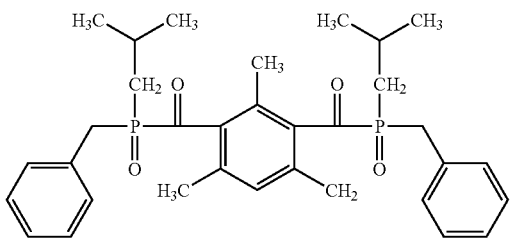

Formula II, R₁=isobutyl, R₃=benzyl, Q=mesitylene, n=1, m=1

120 ml (0.191 mol) buthyllitium were dropped at a temperature of −20° C. to a solution of 8.2 g (0.091 mol) isobutylphosphine in 150 ml tetrahydrofurane. Subsequently 11.2 g (0.0455 mol) 2,4,6-trimethylbenzol-1,3-dicarboxylic acid dichloride diluted with 50 ml tetrahydrofurane were added dropwise at a temperature of 0° C. The reaction mixture was kept at that temperature during 30 min under stirring. Subsequently 15.56 g (0.091 mol) benzylbromide were added dropwise and stirred at the same temperature for 2 hours. Subsequently the reaction mixture was allowed to reach room temperature. The solvent was rotatory evaporated. The residue is taken up in 200 ml toluene. The solution was diluted with water and the layers were separated. 10.3 g (0.091 mol; 30%) hydrogen peroxide were added to the organic phase. After stirring for 2 h, the organic phase was washed with water and with aqueous saturated NaHCO₃, dried over MgSO₄ and filtered. Evaporation and Flash column chromatography (eluent: Hexan/Ethylacetat 3:1) gave the title compound as a viscous resin. ³¹P-NMR 40.04 ppm ¹H-NMR (ppm) 7.13–7.28 (m), 6.76 (s), 3.14–3.41 (m), 2.01–2.0 (d), 1,60–1.97 (m) und 0.89–0.95 (q) determined in CDCl₃.

The following MAPO's may be prepared analogously.

| Product | | Educt |
|---|---|---|
| | | Phenylphosphine<br>2,4,6-Trimethylbenzoylchloride<br>n-Butylbromide |
| Formula II,<br>R₁ = n-butyl, R₃ = phenyl,<br>Q = mesitylylene,<br>n = m = 1. | | |
| | | Phenylphosphine<br>Phthaloyldichloride<br>n-Butylbromide |
| Formula II,<br>R₁ = n-butyl, R₃ = phenyl,<br>Q = o-phenylene,<br>n = m = 1 | | |

| Product | Educt |
|---|---|
| (structure shown) | Phenylphosphine<br>3,3',4,4'benzophenone<br>tetracarboxylic acid<br>dichloride<br>n-Butylbromide |

Formula II,
R₁ = n-butyl, R₃ = phenyl,
Q = 3,3',4,4', benzophenone tetrayl
n = 2, m = 2

3. Preparation of Cyclic Bisacylphosphine Oxide (BAPO)

2-oxo-2-phenyl-2,5-isophosphindole-1,3-dione

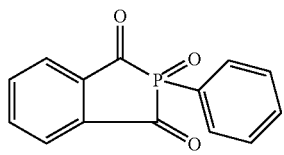

Formula VI, R1 is phenyl, U is isophthaloyl.

120 ml (0.191 mol) buthyllitium were dropped at a temperature of −20° C. to a solution of 10.0 g (0.091 mol) phenylphosphine in 150 ml tetrahydrofurane. A Yellow suspension was obtained. Subsequently 18.4 g (0.091 mol) of phthalic acid chloride diluted with 50 ml tetrahydrofurane were added at a temperature of 0° C. The reaction mixture was stirred at this temperature for 30 minutes and gently warmed up to room temperature with additional stirring for 2 hours. The solvent was evaporated on a rotatory evaporator and the residue diluted with 200 ml of toluene and washed with water.

10.3 g (0.091 mol; 30%) hydrogen peroxide was added to the organic phase. After 2 hours at room temperature, the organic phase was separated, washed with water and with aqueous saturated NaHCO₃, dried over MgSO₄ and filtered. Evaporation of the solvent and flash chromatography gave the title compound.

Application Example

| Weight (g) | Product | Description |
|---|---|---|
| 30.0 | Ebecryl 605 | Epoxyacrylate (UCB) |
| 10.0 | Ebecryl 7100 | Aminoacrylate (UCB) |
| 5.0 | Ebecryl 40 | Propoxylated Pentaerythrol (UCB) |
| 30.0 | OTA 480 | Acrylated trifuntional oligomer based on a glycerol derivative (UCB) |
| 24.0 | TPGDA | Tripropylene glycol diacrylate |
| 0.5 | Ebecryl 1360 | Silicone hexaacrylate |
| 0.5 | Dow Corning 57 | Siliconeadditive, Dow Corning |
| 100.0 | Total OPV Formulation | |

Photoinitiators were investigated with a concentration of 10% and 8% based on 100% weight of the formulation.

For the determination of the cure speed the formulations were applied to white card boards (400 μm) and exposed to the UV light of a medium pressure mercury lamp with a power output of 120 W/cm. The speed of the conveyor belt at which the formulation was completely cured and track free, corresponds to the cure speed.

The results are shown in Table 1

TABLE 1

| Substrate | white cardboard (400 μm) |
|---|---|
| Application equipment | (Erichsen) |
| Layer thickness | 5 μm |
| Lamps | 1 m.p. Hg 120 W/cm (IST) |

| | Cure speed (m/min) | |
|---|---|---|
| | 10% Photoinitiator | 8% Photoinitiator |
| Example 1 | 90 | 50 |
| Example 1.b | 80 | 10 |
| Example 2 | 30 | 15 |

For the determination of the gloss the formulations were applied to chip boards and cured using the UV light of a medium pressure mercury lamp with a power output of 120 W/cm at a conveyor belt speed of 10 m/min. The gloss of the cured films was measured after the samples were post-exposed under a lamp of the type TKL 40/05 for 22 hours.

The results are shown in Table 2.

TABLE 2

| Substrate | chip boards |
| Layer thickness | 100 μm |
| Lamps | 1 m.p. Hg 120 W/cm (IST), TLK 40/05 |
| Cure Speed | 10 m/min |
| Equipment | gloss: Haze-Gloss (Byk-Gardner) |

| | Gloss 20° | |
| --- | --- | --- |
| | 10% Photoinitiator | 6% Photoinitiator |
| Example 1 | 88.00 | 88.00 |
| Example 1.b | 88.00 | |
| Example 2 | 88.00 | 84.00 |

The invention claimed is:

1. Process for the preparation of dimer or multimer forms of BAPO compounds of the formula I,

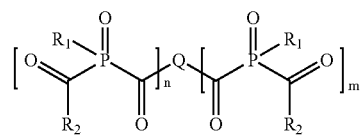

wherein
R$_1$ is unsubstituted or substituted C$_1$–C$_{12}$alkyl, benzyl, C$_1$–C$_{12}$alkoxy or C$_3$–C$_8$cycloalkyl;
R$_2$ is unsubstituted or substituted C$_3$–C$_6$cycloalkyl or C$_5$–C$_{14}$aryl;
Q is a di- tri or tetravalent arylene residue;
n is 1–4, m is 0–2, n+m is 2, 3 or 4,
characterized in that (n+m) equivalents of a dimetalated-phosphine R$_1$P(M)$_2$ are reacted with one equivalent of a di- or polycarboxylic acid halogenide

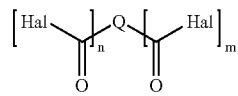

to form an intermediate of the formula III

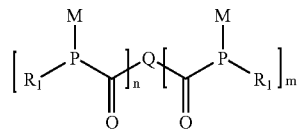

the intermediate III is then reacted with (n+m) equivalents of a further carboxylic acid halogenide (R$_2$—CO-Hal) to form dimer or multimer forms of bisacylphosphine-intermediates of the formula IV

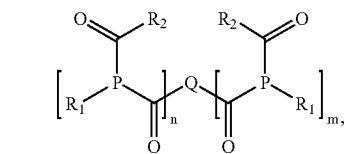

said phosphines IV are then oxidized to form phosphine oxides of the formula I, wherein M is Li, Na or K.

2. Process according to claim 1, wherein M is Li and wherein the process is carried out in an inert atmosphere at a temperature from −20 to 80° C.

* * * * *